(12) United States Patent
Peeler et al.

(10) Patent No.: US 7,708,535 B2
(45) Date of Patent: May 4, 2010

(54) SYSTEMS AND METHODS FOR PROVIDING A DYNAMICALLY ADJUSTABLE RECIPROCATING FLUID DISPENSER

(75) Inventors: Scott C. Peeler, Sandy, UT (US); Brian W. Guest, Farmington, UT (US)

(73) Assignee: ZAxis, Inc., Salt Lake City, UT (US)

( * ) Notice: Subject to any disclaimer, the term of this patent is extended or adjusted under 35 U.S.C. 154(b) by 978 days.

(21) Appl. No.: 10/850,321

(22) Filed: May 19, 2004

(65) Prior Publication Data

US 2005/0013708 A1 Jan. 20, 2005

Related U.S. Application Data

(60) Provisional application No. 60/472,190, filed on May 20, 2003.

(51) Int. Cl.
*F04B 7/06* (2006.01)
*F16H 53/06* (2006.01)

(52) U.S. Cl. .......................... 417/500; 74/569
(58) Field of Classification Search ................. 417/460, 417/500; 92/13; 74/568 M, 568 T
See application file for complete search history.

(56) References Cited

U.S. PATENT DOCUMENTS

| | | | |
|---|---|---|---|
| 3,758,241 A * | 9/1973 | Eheim | 417/494 |
| 4,836,464 A * | 6/1989 | Perego | 242/417.1 |
| 5,020,980 A | 6/1991 | Pinkerton | 417/500 |
| 5,246,354 A * | 9/1993 | Pardinas | 417/500 |
| 2002/0057970 A1* | 5/2002 | Amsler et al. | 417/218 |

* cited by examiner

*Primary Examiner*—Devon C Kramer
*Assistant Examiner*—Philip Stimpert
(74) *Attorney, Agent, or Firm*—David B. Tingey; Kirton & McConkie

(57) ABSTRACT

Systems and methods for providing a dynamically adjustable, synchronously and/or asynchronously reciprocating fluid dispenser. A pump drive motor is coupled to the reciprocating fluid pump to actuate a pump shaft within a pump cylinder, wherein the pump shaft includes a duct that allows fluid to selectively pass thereby within the pump cylinder. As the pump shaft rotates within the pump cylinder, fluid is allowed to enter into a pump bore defined by a portion of the pump cylinder through a pump ingress port. As the pump shaft rotates, it blocks the pump ingress port. Further rotation allows the duct to allow the fluid in the pump bore to be dispensed through a pump egress port. An adjustment motor is coupled to an adjustment mechanism, which selectively adjusts the volume of the pump bore. A controller is coupled to the adjustment motor to dynamically control the adjustment motor, to cause the adjustment mechanism to be precisely and repeatably modified, and/or to control the particular waveform. As such, the volume of fluid dispensed is extremely accurate, repeatable, and dynamic.

19 Claims, 11 Drawing Sheets

SYSTEMS AND METHODS FOR PROVIDING A DYNAMICALLY ADJUSTABLE RECIPROCATING FLUID DISPENSER

RELATED APPLICATIONS

This application claims priority to U.S. Provisional Patent Application Ser. No. 60/472,190 filed May 20, 2003, entitled SYSTEMS AND METHODS FOR PROVIDING A DYNAMICALLY ADJUSTABLE RECIPROCATING FLUID DISPENSER.

BACKGROUND OF THE INVENTION

1. Field of the Invention

The present invention relates to accurately and repeatably dispensing fluid. In particular, the present invention relates to systems and methods for providing a dynamically adjustable, synchronously and/or asynchronously reciprocating fluid dispenser.

2. Background and Related Art

A variety of industries require a safe, accurate handling of fluid. One such industry is the medical industry. By way of example, in the medical industry an assay testing procedure is typically employed to determine whether an infectious disease (e.g., hepatitis or another infectious disease) is present in a particular blood serum. As part of the testing procedure, a biological sample is disposed into a testing receptacle. A reagent is added to the biological sample. In performing the test, it is important that the amount of the biological sample and the amount of the reagent are accurate. In particular, the amount of the reagent added to the biological sample may be in the range of 50 µL-100 µL, with a required accuracy of ±0.5 µL.

The assay testing procedure may further include a variety of separate test receptacles to perform a variety of assay tests to confirm and/or compare results. Some assay testing procedures may include disposing a series of specific reagents.

Valveless, positive displacement pumps have been used in applications that require a safe, accurate handling of fluid. An example of a valveless, positive displacement pump is disclosed in U.S. Pat. No. 4,008,003. While the pump disclosed in U.S. Pat. No. 4,008,003 is an available technique, the pump does not provide an accurate calibration for metering and dispensing fluids. For example, the piston stroke of the pump is not easily adjusted and the angular displacement of the ports cannot be readily calibrated.

Further problems with techniques used in industries that require a safe, accurate handling of fluid include the fact that complex pump designs increase the likelihood for error in manufacturing and assembling the pumps. And, pump designs with moving parts contribute to field failure and maintenance costs.

Thus, while techniques currently exist that are used in industries requiring a safe, accurate handling of fluid, challenges still exist with such techniques, including a requirement for calibration of the fluid-handling device for each surrounding condition, an inability to provide accurate calibration, an increased likelihood for error, an increased likelihood for field failure, increased maintenance costs, and other such challenges. Accordingly, it would be an improvement in the art to augment or even replace current techniques with other techniques.

SUMMARY OF THE INVENTION

The present invention relates to accurately and repeatably dispensing fluid. In particular, the present invention relates to systems and methods for providing a dynamically adjustable, synchronously and/or asynchronously reciprocating fluid dispenser.

Implementation of the present invention takes place in association with a reciprocating fluid pump. A pump drive motor is coupled to the reciprocating fluid pump to actuate a pump shaft within a pump cylinder, wherein the pump shaft includes a cut out portion (duct) that allows fluid to selectively pass thereby within the pump cylinder. As the pump shaft rotates within the pump cylinder, fluid is allowed to enter into a pump bore defined by a portion of the pump cylinder through a pump ingress port. As the pump shaft rotates, it blocks the pump ingress port. Further rotation allows the duct to allow the fluid in the pump bore to be dispensed through a pump egress port. This process may be repeated for subsequently dispensing volumes of fluid using the reciprocating fluid pump.

Implementation of the present invention further includes an adjustment motor (e.g., a linear actuator, etc.) that is coupled to an adjustment mechanism, which selectively adjusts the volume of the pump bore. In at least one implementation, the volume of the pump bore is adjusted as the angle of the pump shaft is modified. A modification of the angle changes the stroke of the pump shaft. In another implementation, the volume of the pump bore is adjusted through a system of gears to selectively change the stroke of the pump shaft. Further, at least some implementations allow for synchronous and/or asynchronous reciprocation.

Further implementation includes a controller coupled to the adjustment motor to dynamically control the adjustment motor to cause the adjustment mechanism to be precisely and repeatably modified. As such, the volume of fluid dispensed is extremely accurate, repeatable, and dynamic. Moreover, a controller may be used to provide control over the particular waveform of a synchronously and/or asynchronously reciprocating fluid dispenser.

As the methods and processes of the present invention have proven to be useful in the area of dynamically dispensing fluid, those skilled in the art can appreciate that the methods and processes can be used in a variety of different applications, in a variety of different areas of manufacture to yield, and embrace a variety of different kinds of fluids. Examples of such industries include the medical industry, the industrial industry, the electronics industry, the food industry, the dairy industry, the precision cleaning industry, the cosmetic industry, the hygene industry, etc. Examples of such fluids include adhesives, lubricants, chemicals, drugs, paints, pigments, resins, solvents, epoxies, inks, ceramic slurries, solutions, candy coatings, polishes, flavorings, food preservations, cleaning agents, pigments, fragrances, gases, liquids, ets.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

Figure 1:
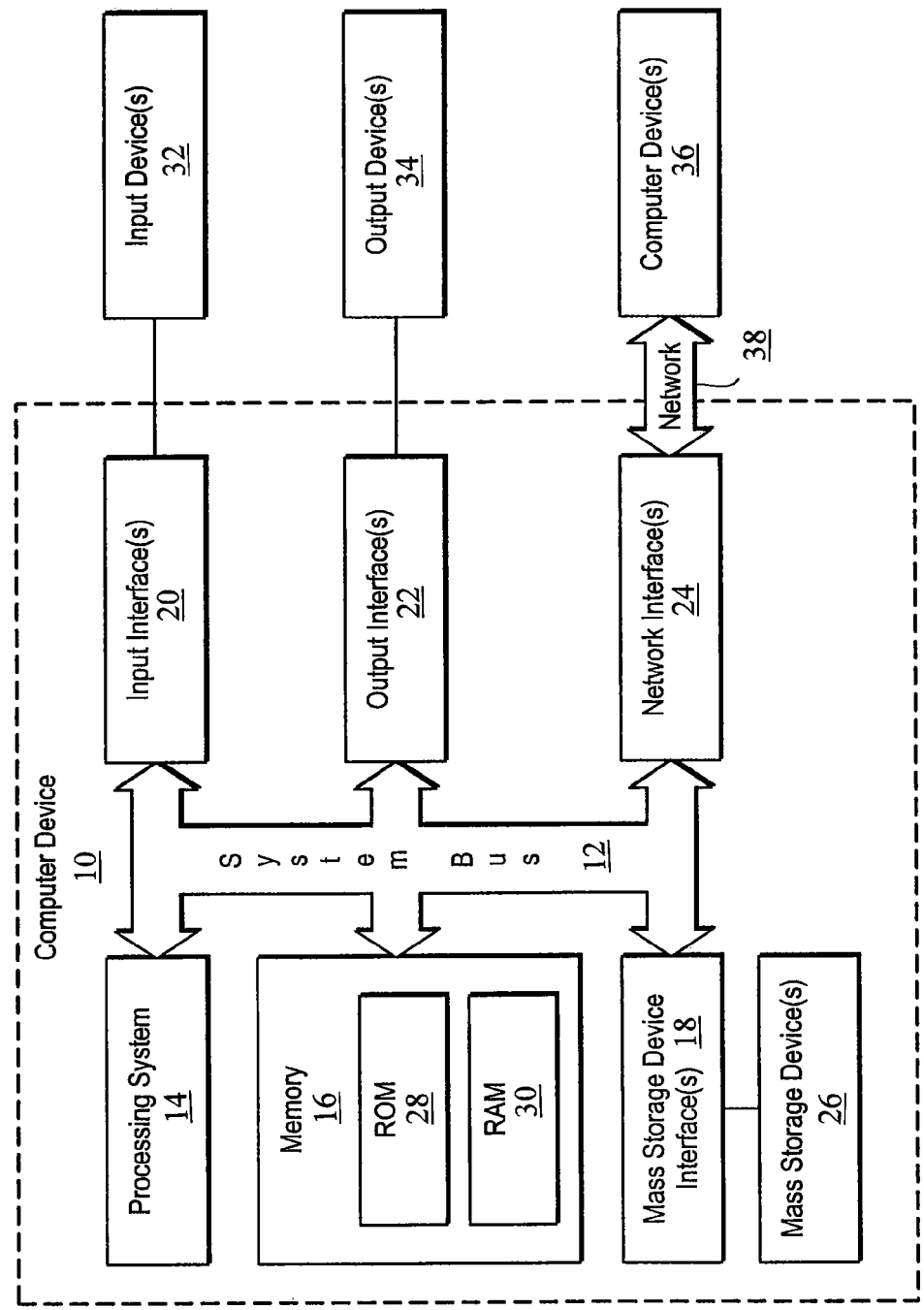
FIG. 1 illustrates a representative computer device for use in association with at least some of the embodiments of the present invention.

The present invention relates to accurately and repeatably dispensing fluid. In particular, the present invention relates to systems and methods for providing a dynamically adjustable, synchronously and/or asynchronously reciprocating fluid dispenser.

Embodiments of the present invention take place in association with a reciprocating fluid pump. In at least one embodiment, a pump drive motor is coupled to the reciprocating fluid pump to actuate a pump shaft within a pump cylinder, wherein the pump shaft includes a duct that allows fluid to selectively pass thereby within the pump cylinder. As the pump shaft rotates within the pump cylinder, fluid is allowed to enter into a pump bore defined by a portion of the pump cylinder through a pump ingress port. As the pump shaft rotates further, the shaft blocks the pump ingress port. Further rotation allows the duct of the shaft to allow the fluid in the pump bore to be dispensed through a pump egress port. This process may be repeated for subsequently dispensing volumes of fluid using the synchronously and/or asynchronously reciprocating fluid pump.

Further embodiments of the present invention include an adjustment motor (e.g., a linear actuator, etc.) that is coupled to an adjustment mechanism, which selectively adjusts the volume of the pump bore. In at least one embodiment, the volume of the pump bore is adjusted as the angle of the pump shaft is modified. A modification of the angle changes the stroke of the pump shaft. In another embodiment, the volume of the pump bore is adjusted through a system of gears to selectively change the stroke of the pump shaft.

Further embodiments of the present invention includes a computer device (e.g., a controller or another computer device) that is coupled to the adjustment motor to dynamically control the adjustment motor and cause the adjustment mechanism to be precisely and repeatably modified. As such, the volume of fluid dispensed is extremely accurate, repeatable, and dynamic, as will be further discussed below.

In some embodiments, a controller is used to provide control over the particular waveform and to allow for any type of a waveform to be used (e.g., sine wave, square wave, pulse, etc.).

The following disclosure of the present invention is grouped into two subheadings, namely "Representative Computer Device" and "Providing a Dynamically Adjustable Reciprocating Fluid Dispenser." The utilization of the subheadings is for convenience of the reader only and is not to be construed as limiting in any sense.

Representative Computer Device

As provided above, at least some embodiments of the present invention include a controller that is coupled to an adjustment motor and/or another component of the fluid dispensing system. One such example of a controller is a computer device. Accordingly, a discussion is provided relating to a representative computer device. A computer device coupled to the adjustment motor enables dynamic control of the adjustment motor and causes the adjustment mechanism to be precisely and repeatably modified. As such, the volume of fluid dispensed is extremely accurate, repeatable, and dynamic. Further, a computer device can be used to control the particular wave form.

Accordingly, FIG. 1 and the corresponding discussion are intended to provide a general description of a representative computer device. One skilled in the art will appreciate that the invention may be practiced by one or more computing devices and in a variety of system configurations, including in a networked configuration.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative computer device is illustrated as computer device 10, which may be a general-purpose or special-purpose computer. For example, computer device 10 may be a personal computer, a notebook computer, a personal digital assistant ("PDA") or other hand-held device, a workstation, a minicomputer, a mainframe, a supercomputer, a multi-processor system, a network computer, a controller, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, selectable buttons or dials, a scanner, a camcorder, a digital camera, and the like. Similarly, examples of input interfaces 20 that may be used to connect the input devices 32 to the system bus 12 include a serial port, a parallel port, a game port, a universal serial bus ("USB"), a firewire (IEEE 1394), or another interface.

One or more output interfaces 22 may be employed to connect one or more corresponding output devices 34 to system bus 12. Examples of output devices include a monitor or display screen, a speaker, a printer, a motor or actuator, and the like. A particular output device 34 may be integrated with or peripheral to computer device 10. Examples of output interfaces include a video adapter, an audio adapter, a parallel port, other output interfaces, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Providing a Dynamically Adjustable Reciprocating Fluid Dispenser

As provided above, embodiments of the present invention relate to accurately and repeatably dispensing fluid. In particular, embodiments of the present invention embrace systems and methods for providing a dynamically adjustable, synchronously and/or asynchronously reciprocating fluid dispenser.

Figure 2:
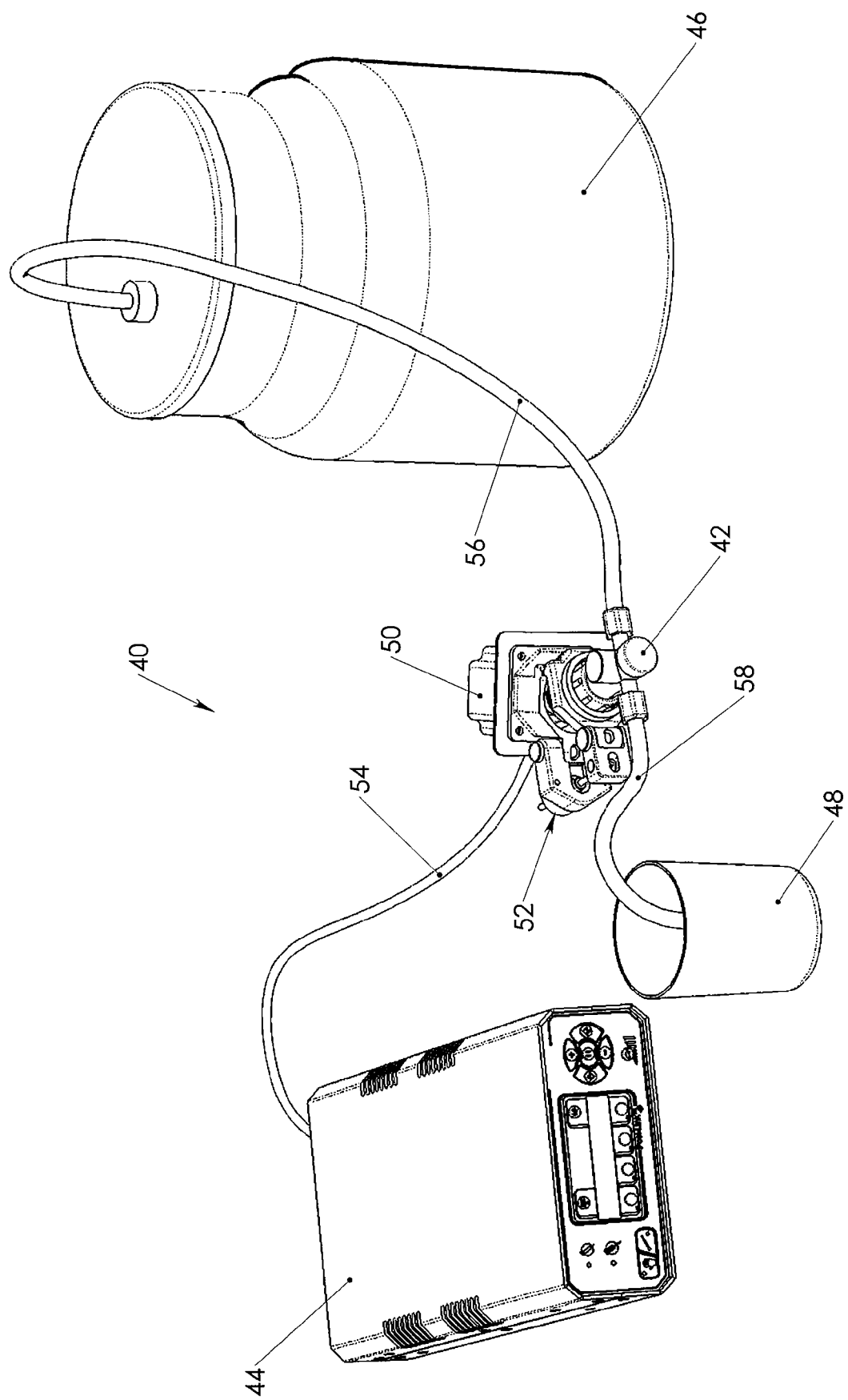
FIG. 2 illustrates a representative system in association with the present invention for dynamically dispensing fluid.

With reference to FIG. 2, a representative system is illustrated for dynamically dispensing fluid in association with an embodiment of the present invention. In FIG. 2, a rotating reciprocating pump system 40 is illustrated with a micro-stepping motor adjustment. System 40 includes pump 42, pump controller 44, a fluid source or reservoir 46, dispense target 48, pump drive motor 50, micro-stepping motor 52, electrical coupler 54, coupler 56, and coupler 58. Pump controller 44 is electronically coupled to pump drive motor 50, which is coupled to reciprocating pump 42, and to micro-stepping motor 52, which is coupled to an adjustment mechanism. Fluid source 46 is coupled to an ingress port of pump 42 and dispensing target 48 is associated with an egress port of pump 42.

Figure 3:
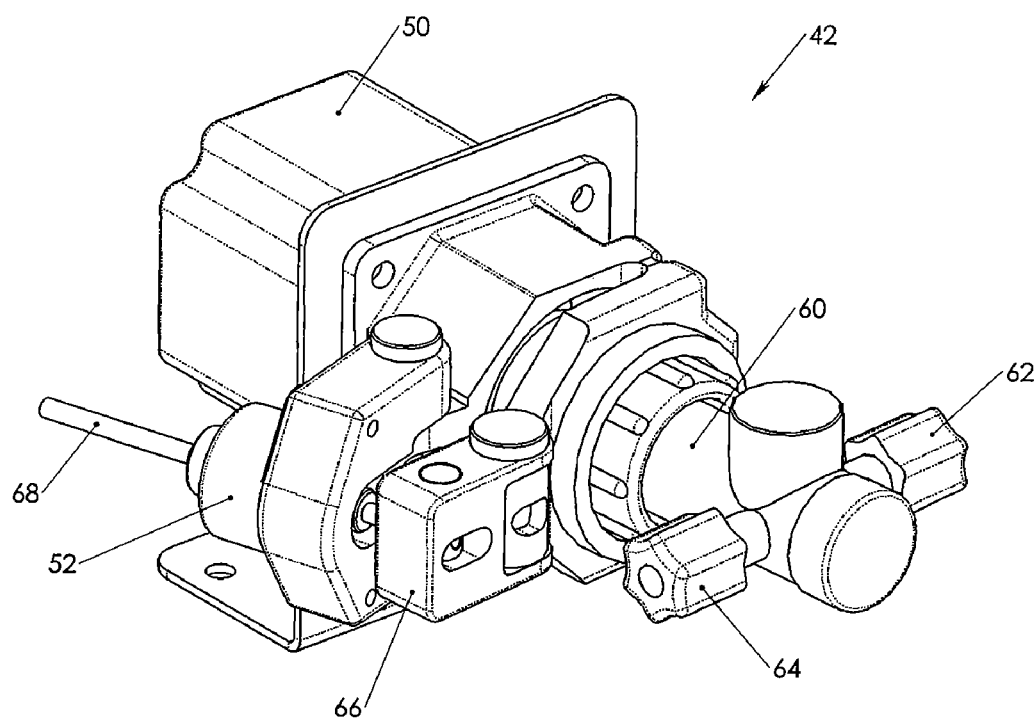
FIG. 3 illustrates a representative reciprocating fluid dispenser having a parallel linear actuator and a non-captive screw, wherein the adjustment mechanism is in a closed position.

FIG. 3 illustrates a representative reciprocating fluid dispenser having a parallel linear actuator and a non-captive screw, wherein the adjustment mechanism is in a closed position. In particular, FIG. 3 provided pump 42 having pump drive motor 50, micro-stepping motor 52, cylinder bore 60, ports 62-64, component 66, and non-captive screw 68. An adjustment mechanism, comprising micro-stepping motor 52, component 66 and non-captive screw 68, allows for a controlled and repeatable adjustment of the angle of cylinder bore 60, and thus a controlled and repeatable adjustment of the stroke of the pump shaft. Further, the adjustment mechanism allows for pre-set shot steps or sizes, an automatic adjustment of the shot size, and instantaneous adjustment of the shot size, and dynamic and repeatable control.

Figure 4:
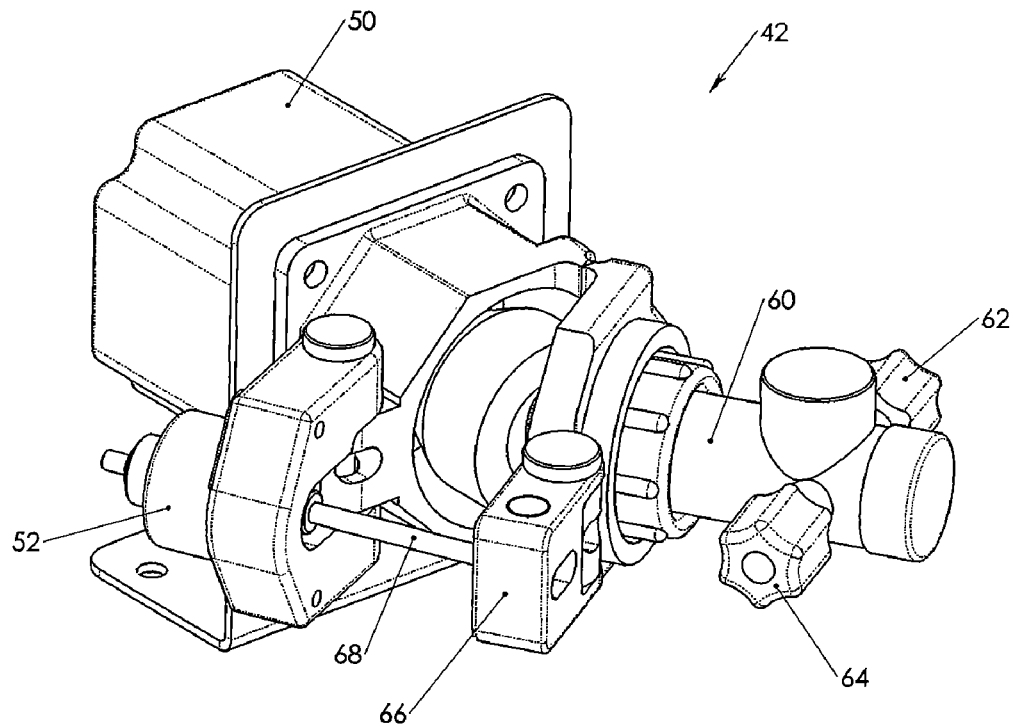
FIG. 4 illustrates the representative reciprocating fluid dispenser of FIG. 3, wherein the adjustment mechanism is in an open position.

In FIG. 3, the adjustment mechanism is illustrated in a closed position. With reference now to FIG. 4, the representative reciprocating fluid dispenser of FIG. 3 having a parallel linear actuator and a non-captive screw, wherein the adjustment mechanism is in an open position.

Figure 5:
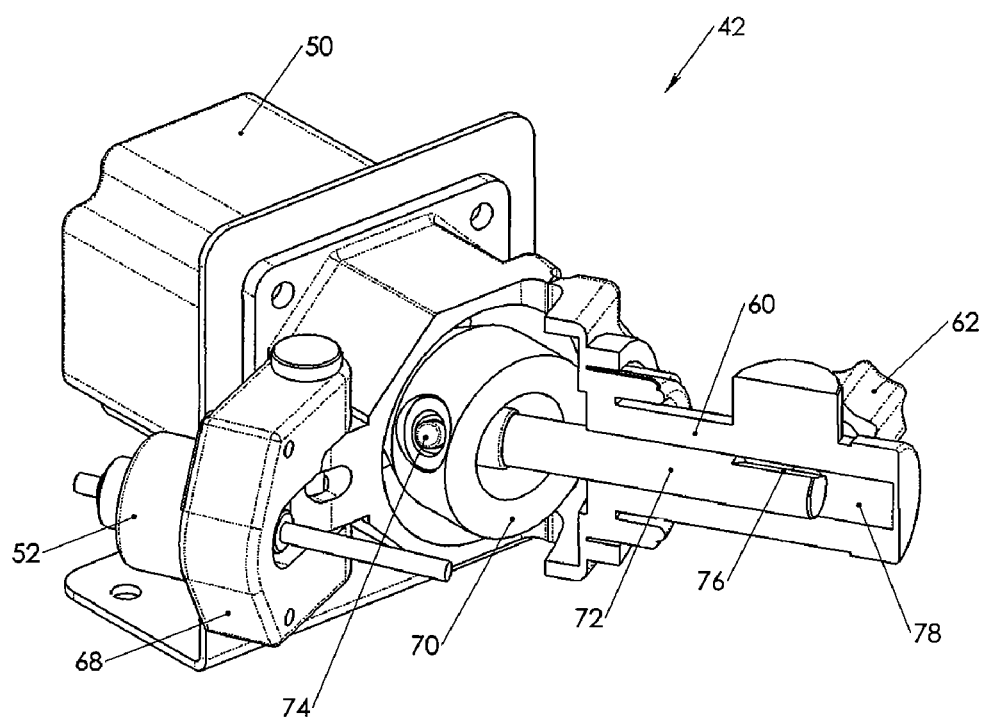
FIG. 5 illustrates the representative reciprocating fluid dispenser of FIG. 4 with the pump shaft in a first position.
Figure 6:
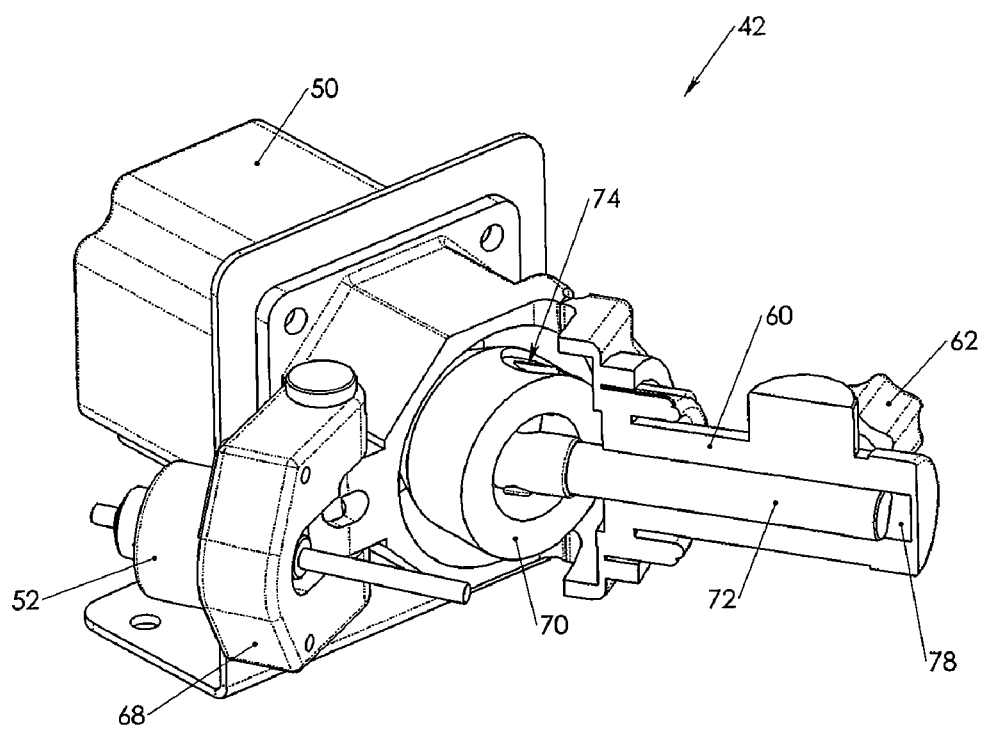
FIG. 6 illustrates the representative reciprocating fluid dispenser of FIG. 4 with the pump shaft in a second position.

FIG. 5 illustrates a representative reciprocating fluid dispenser having cylinder bore in a crossectional view to illustrate receiver 70, piston 72, pin 74, duct 76, and stroke size 78. Receiver 70 includes an aperture configured to receive pin 74, which is coupled to piston 72. As receiver rotates, piston (pump shaft) 72 moves linearly within cylinder bore 60 between a first or recessed position (FIG. 5) and a second or extended position (FIG. 6). The volume between piston 72 in a recessed position and the end of cylinder bore 60 determines stroke size 78. The rotation of duct 76 allows for fluid to selectively enter into cylinder bore 60.

FIG. 6 illustrates the representative reciprocating fluid dispenser of FIG. 5 with receiver 70 in a rotated position and piston 72 in an extended position to dispense the fluid in cylinder bore 60.

Figure 7:
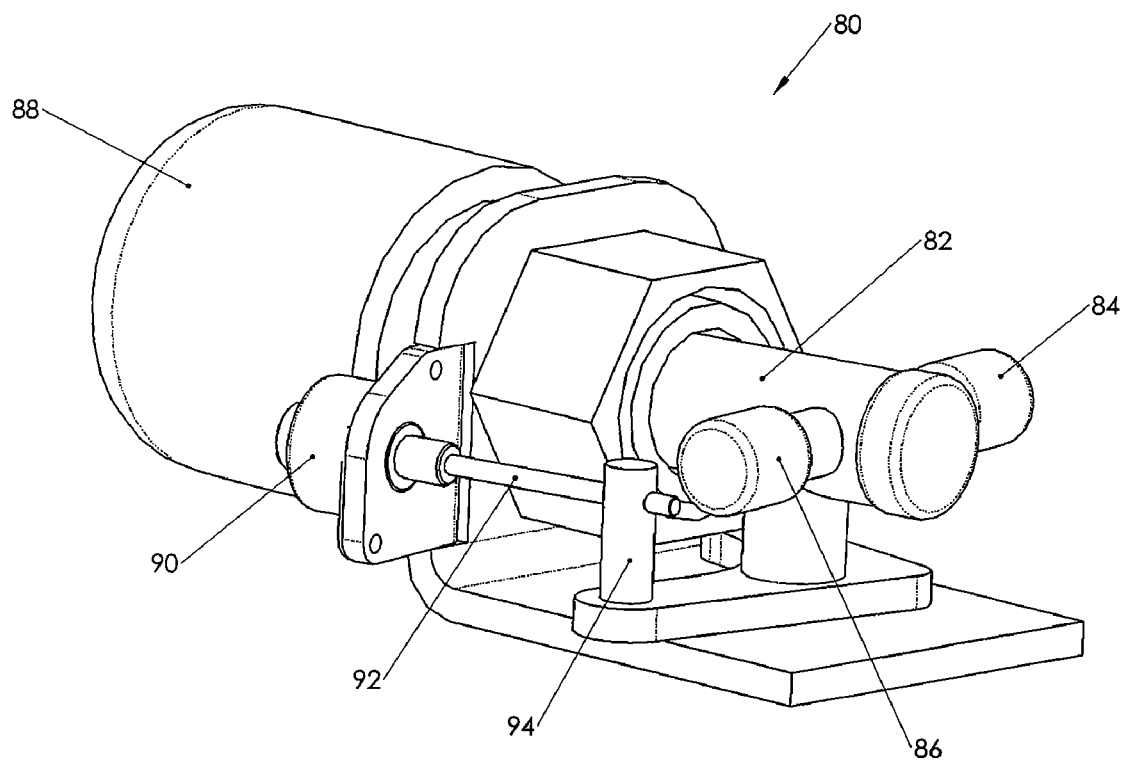
FIG. 7 illustrates a representative reciprocating fluid dispenser having a parallel linear actuator and a captive screw.

With reference now to FIG. 7, a representative reciprocating fluid dispenser is illustrated that includes a parallel linear actuator and a captive screw. In FIG. 7, pump 80 includes cylinder bore 82, ports 84-86, pump drive motor 88, and an adjustment mechanism comprising linear actuator 90, captive screw 92 and component 94. As component 94 is positioned toward linear actuator 90, cylinder bore 82 is placed in a first or closed position. Alternatively, as component 94 is selectively moved away from linear actuator 90, an angle is formed in relation to cylinder bore 82 and pump drive motor 88 to cause cylinder bore 82 to be in an open position.

Figure 8:
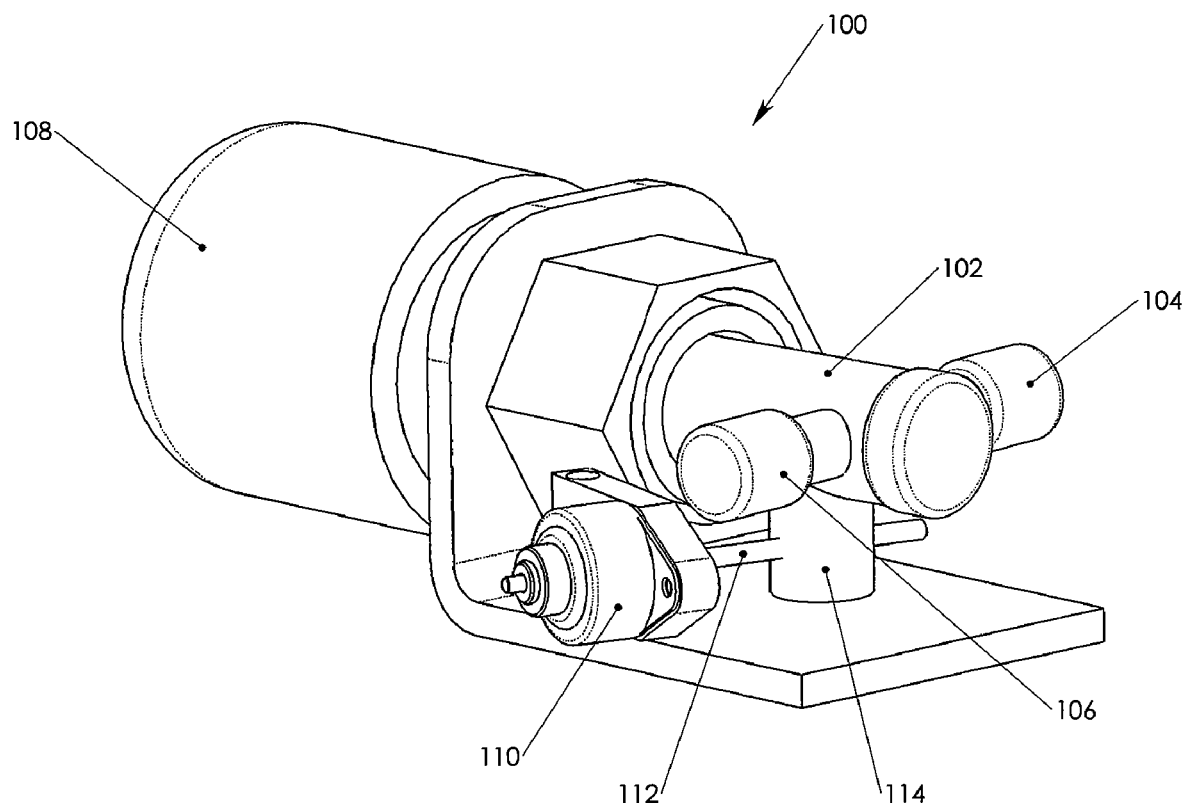
FIG. 8 illustrates a representative reciprocating fluid dispenser having a linear actuator and a captive screw.

With reference now to FIG. 8, a representative reciprocating fluid dispenser is illustrated having a linear actuator and a captive screw. In FIG. 8, pump 100 includes cylinder bore 102, ports 104-106, pump drive motor 108, and an adjustment mechanism, which comprises linear actuator 110, captive screw 112 and component 114. In the embodiment of FIG. 8, linear actuator 110 is selectively driven toward component 114 or away from component 114 to transition cylinder bore between one of an open and closed position in order to adjust the stroke size.

As illustrated in the representative embodiments of FIGS. 2-8, embodiments of the present invention embrace a reciprocating fluid pump. A pump drive motor is coupled to the reciprocating fluid pump to actuate a pump shaft within a pump cylinder, wherein the pump shaft includes a duct that allows fluid to selectively pass thereby within the pump cylinder. As the pump shaft rotates within the pump cylinder, fluid is allowed to enter into a pump bore defined by a portion of the pump cylinder through a pump ingress port. As the pump shaft rotates, it blocks the pump ingress port. Further rotation allows the cut out portion to allow the fluid in the pump bore to be dispensed through a pump egress port. This process may be repeated for subsequently dispensing volumes of fluid using the reciprocating fluid pump.

At least some embodiments include an adjustment motor (e.g., a linear actuator, etc.) that is coupled to an adjustment mechanism, which selectively adjusts the volume of the pump bore. In at least one embodiment, the volume of the pump bore is adjusted as the angle of the pump shaft is modified. A modification of the angle changes the stroke of the pump shaft. As will be discussed below, in at least some embodiments, the adjustment mechanism comprises a gear system.

A controller is coupled to the adjustment motor to dynamically control the adjustment motor to cause the adjustment mechanism to be precisely and repeatably modified. As such, the volume of fluid dispensed is extremely accurate, repeatable, and dynamic.

Figure 9:
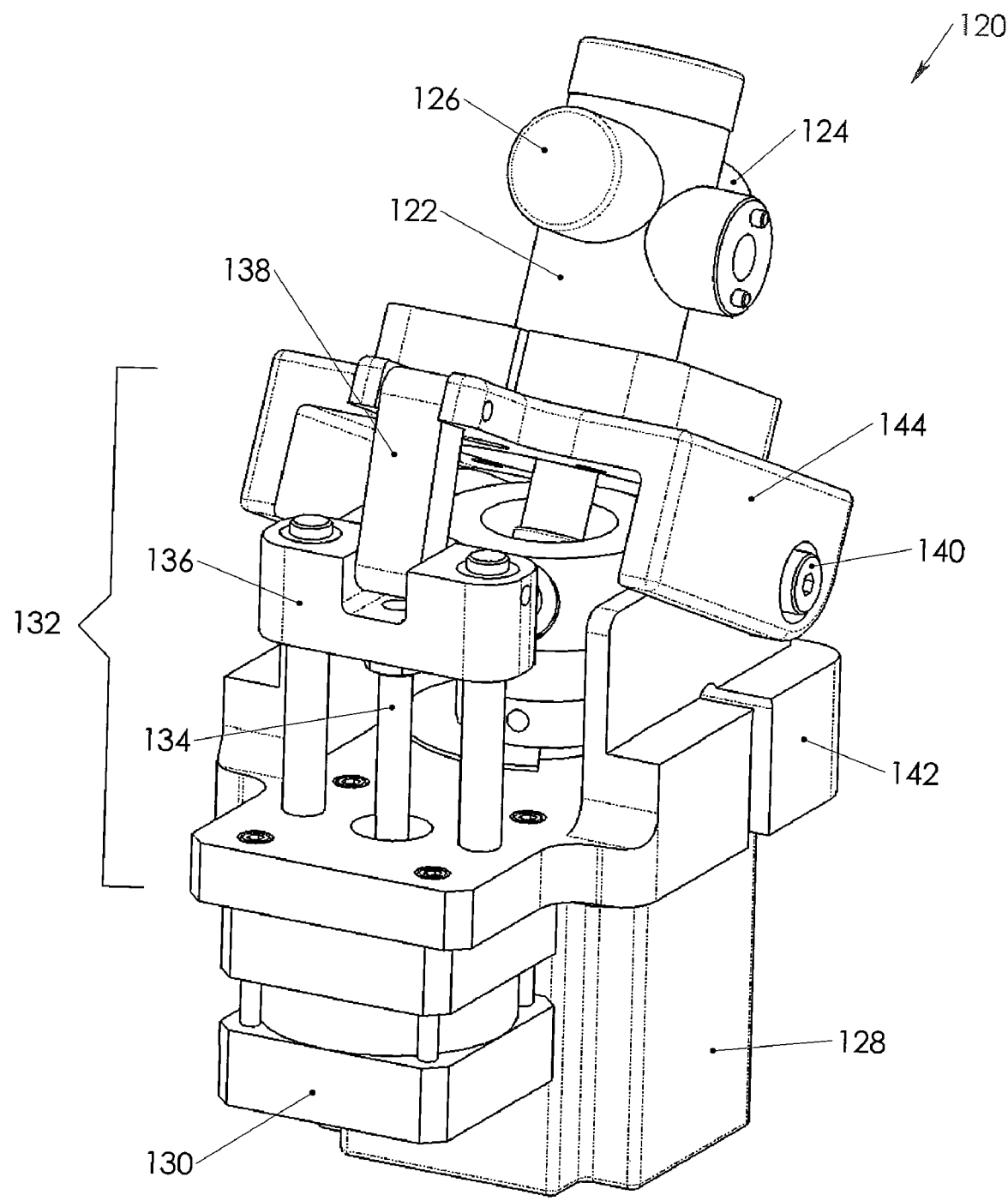
FIG. 9 illustrates a representative reciprocating fluid dispenser having a pillow block.

With reference now to FIG. 9, a representative reciprocating fluid dispenser having a pillow block is illustrated. In FIG. 9, pump 120 includes cylinder bore 122, ports 124-126, pump drive motor 128, linear actuator 130 and adjustment mechanism 132. Wherein adjustment mechanism 132 comprises linear actuator 130, screw 134, pillow block 136, coupler 138 and hinge block pivot point 140. Pump 120 further includes a sealer 142 and piston 144. As receiver 142 rotates, piston 144 moves within cylinder bore 122 between a recessed position and an extended position to cause the fluid to be precisely received and dispensed. As adjustment mechanism 132 transitions pump 120 between a closed position and an open position, the stroke size is adjusted.

Figure 10:
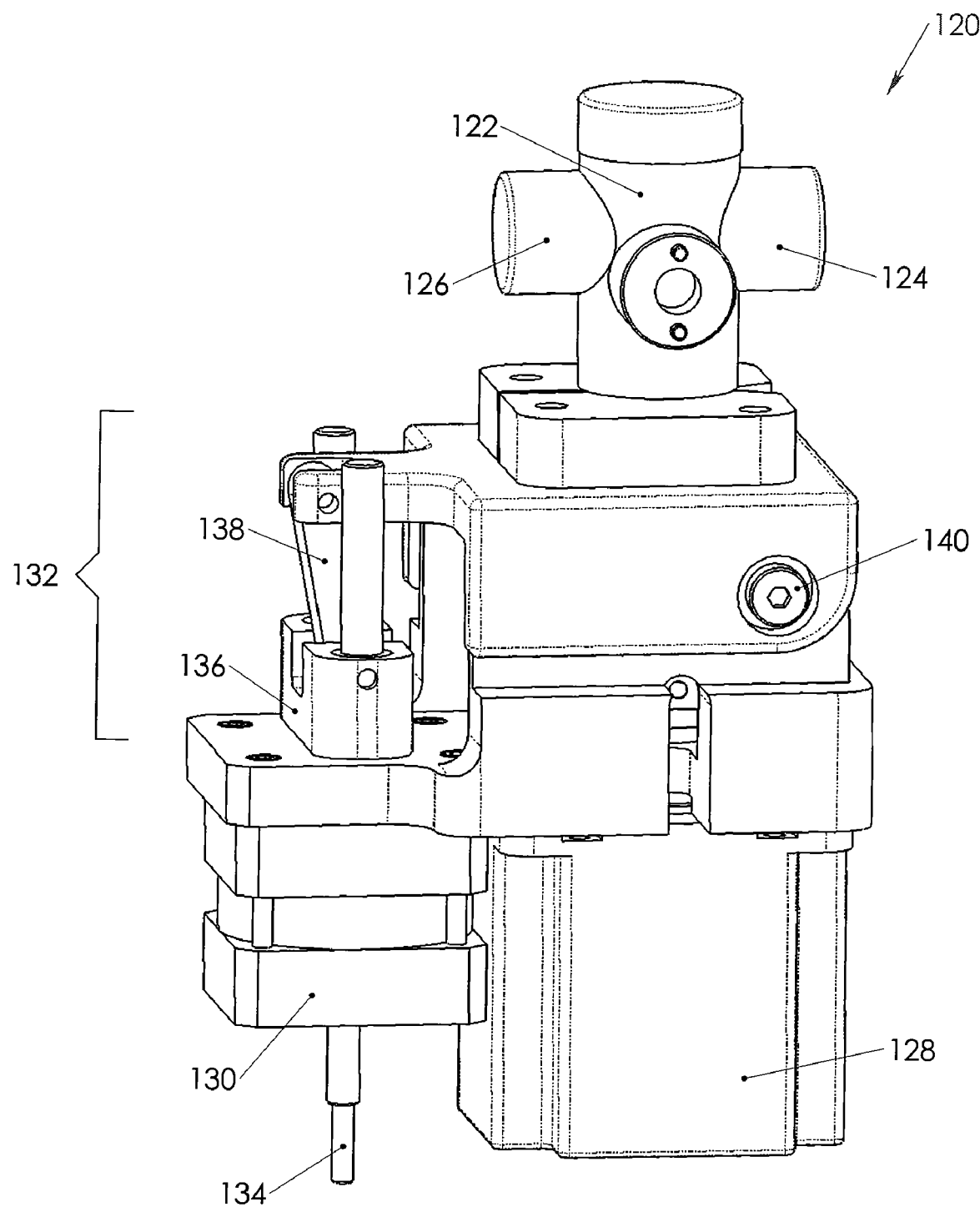
FIG. 10 illustrates the representative reciprocating fluid dispenser of FIG. 9, wherein the adjustment mechanism is in a closed position.
Figure 11:
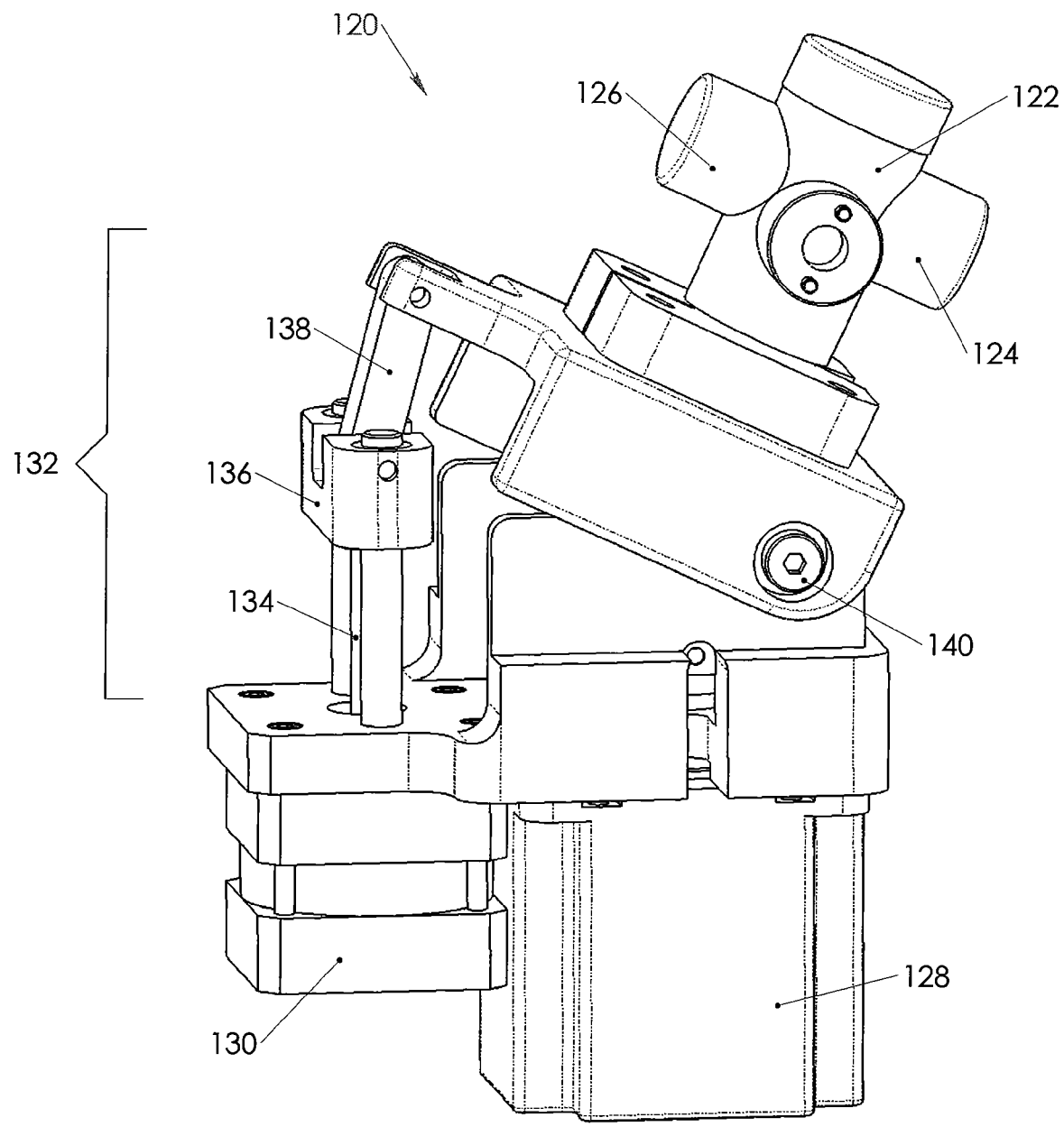
FIG. 11 illustrates the representative reciprocating fluid dispenser of FIG. 9, wherein the adjustment mechanism is in an open position

With reference to FIG. 10, pump 120 is illustrated in a closed position. With reference now to FIG. 11, pump 120 is illustrated in an open position. As illustrated in the combination of FIGS. 10 and 11, the driving of screw 134 by linear actuator 130 transitions pump 120 about hinge block pivot point 140.

Figures 12, 13:
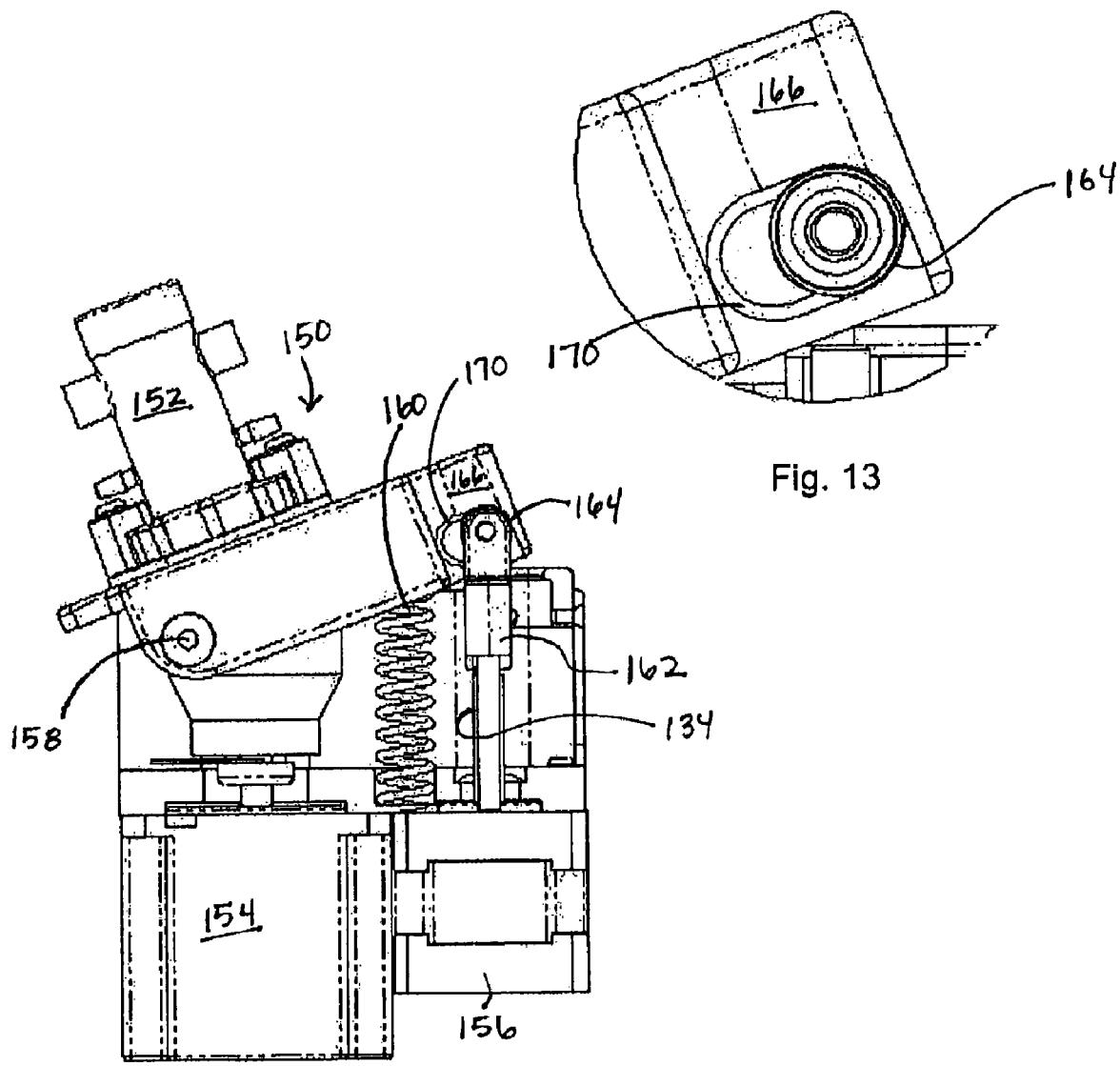
FIG. 12 illustrates another representative reciprocating fluid dispenser having a pillow block.
FIG. 13 illustrates additional detail relating to a portion of the representative reciprocating fluid dispenser of FIG. 12.

With reference now to FIG. 12, another representative reciprocating fluid dispenser is illustrated. In FIG. 12, pump 150 includes cylinder bore 152, pump drive motor 154 and an adjustment mechanism comprising linear actuator 156, hinge block pivot point 158, spring 160, pillow block 162, cam follower 164 and hinge block 166. Spring 160 provides an ongoing bias on hinge block 166 to further enhance precision in dispensing fluid. Pillow block or sleeve element 162 moves freely along two linear guide rods. Linear actuator 156 includes a lead screw that is threaded into the center of pillow block 162 and has a lock nut to prevent loosening. Linear actuator 156 controls the position of pillow block 162.

With reference to FIG. 13, additional detail relating to a portion of the representative reciprocating fluid dispenser in FIG. 12 is provided. In FIG. 13, a surface 170 of hinge block 166 is provided to allow a cam to run against surface 170. With reference back to FIG. 12, cam follower 164 runs on a lower surface and the control feature. Upward pressure from spring 160 compensates for the clearance between cam follower 164 and the control surface. Upward pressure or bias by spring 160 also compensates for any backlash in the linear actuator.

One representative system includes a user-friendly electronically programmable controller and a superior metering head. A linear stepper actuator makes ultra-fine adjustments to the angle of the pump, thereby changing the quantity of metered liquid. This technology employs diamond honing and internal modifications to provide enhanced fluidic movement of solutions varying in viscosity and surface tension. A representavie pump of the system is valveless and when combined with the electronic controller, the system can achieve a high degree of accuracy when metering fluids.

Controlling the synchronized rotating and reciprocating movement allows the controller to accurately maintain the displacement of the piston. The pump assembly is manufactured to extremely tight tolerances, insuring accuracy and repeatability. This pump eliminates a need for external supply and discharge valves. One port of the pump is open while the other is closed and visa-versa, hereby never allowing both ports to interconnect.

In some embodiments, the valveless pumping function is accomplished by the synchronous rotation and reciprocation of a ceramic piston in a precisely mated ceramic cylinder bore or liner. One complete piston revolution is required for each suction/discharge cycle as shown. The piston bottoms for maximum fluid and bubble clearing. Moving the pump head position changes the piston stroke length and in turn the flow rate. Flow rate indication through the controller provides for accurate and simple linear calibration. As an inlet port is sealed and the pump chamber or bore is full, the outlet port opens up. The piston rotates and reciprocates. As the piston is pulled back and the piston flat opens to the inlet port, suction is created and fluid fills the pump chamber. As the piston reaches the highest point in the reciprocation cycle, the pump chamber is now at its maximum volume capacity. Continuing the rotation, the inlet port is then sealed. Continuing the rotation and reciprocation, the piston is forced down and the piston flat/duct opens to the outlet port. Discharge is created and fluid is pumped out. The piston bottoms for maximum fluid and bubble clearing. Continuing the rotation, the outlet port is then sealed and crossover occurs. As the outlet port is sealed and the pump chamber is empty, the inlet port opens to start another suction stroke. Accordingly, only one moving part is in contact with the fluid—the piston. Such embodiments provide adjustable displacement, low dead volume, low liquid sheer, self-priming, resistance to abrasion, reversibility, valueless operation and/or self-sealing.

In at least some embodiments, solid-state electronics with microprocessor controls provide forward and reverse fluid movement, as well as linear adjustable rate control, volume select, prime and meter modes. Some embodiments further include multiple channels, PLC interfacing, optional RS 232 communication, alarm systems and/or cycle outputs.

A metering head is in-line with the fluid path and may be detached for ease of cleaning and autoclaving. The metering head is a piston/cylinder arrangement utilizing positive displacement. The heart of the metering head is the piston.

In one embodiment, the pump is mounted in a vertical position with the discharge port up and the suction port down to allow any air bubbles that enter the pumping chamber to directly exit through buoyancy assistance.

Representative applications for embodiments of the present invention embrace the medical industry (e.g., dispensing, aspirating, rinsing, and mixing systems, for syringe pump replacement in diagnostic, clinical chemistry, dialysis and medical equipment manufacturing, dispensing adhesives and lubricants used in assembly of disposable medical components, etc.), the industrial industry (e.g., metering and mixing paint and pigment additives, catalyst for foundry resins, plating bath regeneration, petroleum additives, photo chemicals, inks, monomers, adhesives, etc.), the instrumentation industry (e.g., for all kinds of precision instruments and monitors including, titrators, TOC, SO2 monitors, chromatographic systems, humidity control, etc.), the precision cleaning industry (e.g., for metering of concentrated cleaning agents used in automated washers for laboratory glassware and mechanical components, the metering of ultra concentrated liquid car wash detergents, etc.), the automotive industry (e.g., in hydrogen fuel cell research and development for both the humidification and fuel injection systems, for metering insulating and encapsulating coating materials in the manufacture of stators, armatures, and distributors, to verify gasoline octane rating, etc.), the battery manufacturing industry (e.g., for precision metering of electrolytes and slurries into batteries, for lubrication of fine blanking machines used to form and stamp battery components, etc.), the cosmetic and hygienic industry (e.g., for precision metering of pigments used in cosmetic color mixing systems, moisture control and fragrance addition in the manufacture of diapers and sanitary napkins, etc.), the electronics industry (e.g., for metering of ceramic slurries in the manufacture of capacitors and diodes, the metering of insulating and encapsulating materials used in electric motor manufacture, addition of flux for wave soldering equipment, metering of mercury for switch manufacturing, metering of semiconductor wash and etch solutions, etc), the pilot plant industry (e.g., for research, development, and testing of a wide range of process applications including chemical synthesis, water and waste treatment, power plants, pharmaceutical manufacturing, petroleum refining, photo finishing, etc.), the environmental industry (e.g., for sampling of stack gases, ground water, and wastewater, as well as injection of monomers, polymers, and treatment chemicals for water and waste, TCLP, etc.), the food industry (e.g., for candy coating and polishing, vitamin fortification for milk, addition of flavors, colors, and preservatives, hops for brewing and sanitizing agents for aseptic packaging, sample and reagent fluid control in milk analyzers and other food quality control instrumentation, etc., the spraying industry, (e.g., for the injection of insecticides, herbicides, and agricultural nutrients, ULV spray equipment for mosquito control, the metering industry (e.g., for metering of solvents, UV adhesives, lubricants, reagents, and mercury in the manufacture of medical disposable components, electronics, pharmaceuticals, computers, calibration equipment, etc.), and other industries.

Figure 14:
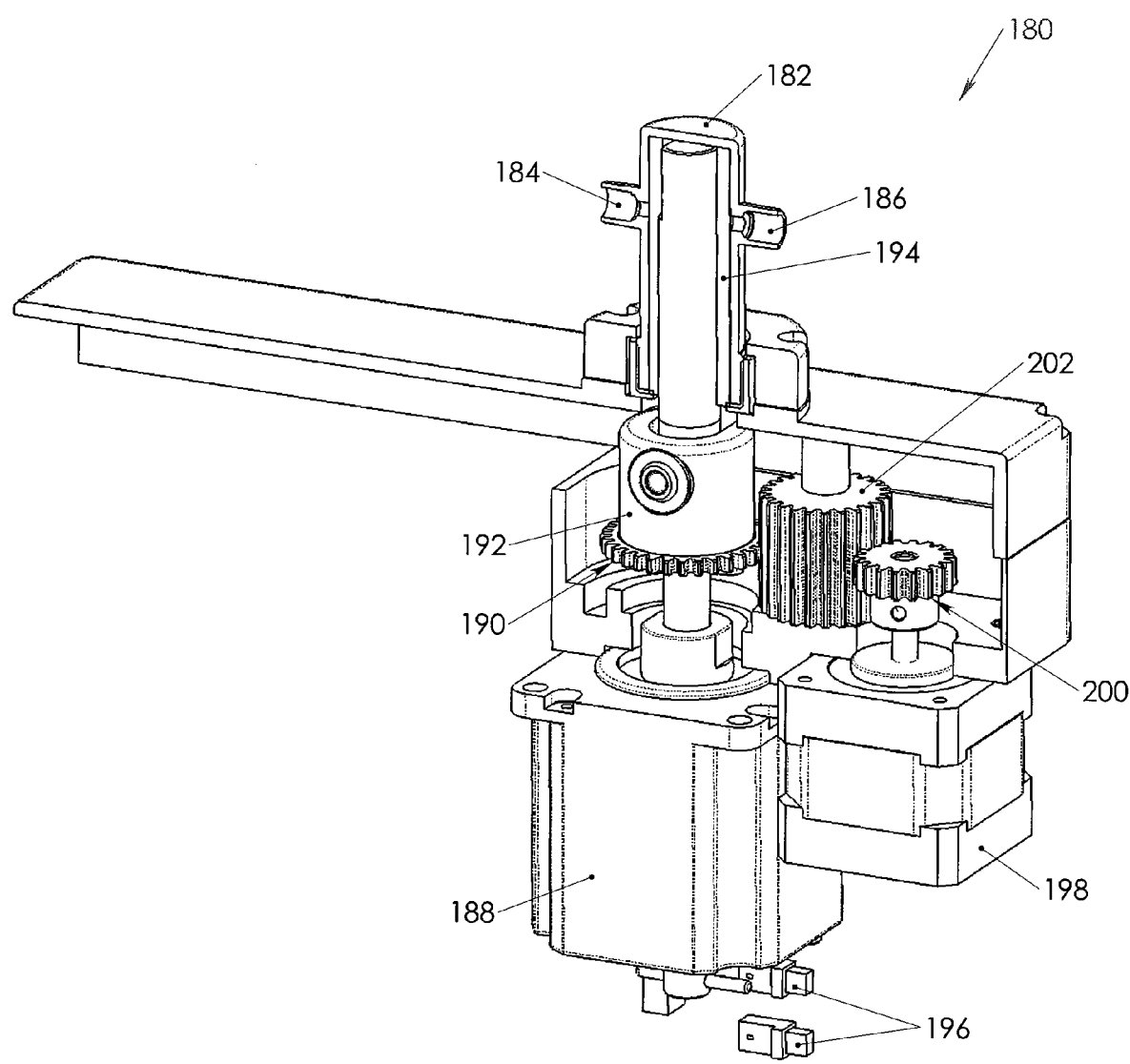
FIG. 14 illustrates a representative reciprocating fluid dispenser having a gear system.

With reference now to FIG. 14, a representative synchronously and/or asynchronously reciprocating fluid dispenser is provided. In FIG. 14, pump 180 includes cylinder bore 182, ports 184 and 186, pump drive motor 188, piston thrust gear 190, thrust gear spindle mechanism 192, reciprocating piston 194, linear travel sensors 196, linear actuator 198, drive gear 200, and idler gear 202.

In one embodiment, pump 180 is synchronous to electronics that operates pump drive motor 188 and linear actuator 198 simultaneously in a synchronous fashion to provide a rotating reciprocating pump. Thus, in one embodiment the pump drive motor 188 is used to rotate piston 194 so as to be aligned with an inlet port, such as port 184. In the actuator 198 is then used to pull back on the piston 194 so that the fluid may enter into cylinder bore 182. Pump drive motor 188 is then used to rotate piston 194 so as to be aligned with an outlet port, such as port 186. In the actuator 198 is then used to cause the piston 194 to dispense the fluid from cylinder bore 182. In a further embodiment, utilization of the two motors to rotate the piston and cause the piston to move up and down is performed at the same time. Accordingly, piston 194 is rotated and pulled back at the same time to perform a similar function as a wobble function of the embodiments illustrated in FIGS. 5-6. As such, rather than having a mechanical wobble function, the function is performed electronically. Thus, the rotating reciprocating fluid dispenser is configured to perform a wobble-like function electronically to provide a synchronous reciprocating fluid dispenser or alternatively each function may be performed such as to provide, synchronous and asynchronous reciprocating fluid dispenser.

In one embodiment, idler gear 202 acts as an anti-rotation device. Idler gear 202 performs one revolution in the same time that it takes piston thrust gear 190 to travel the length of idler gear 202. This provides a representative synchronous reciprocating fluid dispenser, since idler gear 202 is rotating at the same time that linear actuator 198 performs or initiates the pumping action.

In at least some embodiments of the present invention, a control may be used to adjust the pulses rather than just being tied to one motor that performs the pumping action. Further, in accordance with at least some embodiments of the present invention, controls provided to utilize any type of wave form, including a pulse, a square wave, a sine wave, etc. Further, compensation is allowed during the process of reciprocation. In one embodiment control over a wave form is provided because of the ability to turn to one port or the other without drawing or pushing fluid and then drawing or pushing the fluid at any time as the piston rotates at any speed or any wave form.

Accordingly, at least some embodiments of the present invention embrace a spherical bearing and hub arrangement that is adjusted electronically to provide a reciprocating fluid dispenser. Other embodiments embrace inclusion of an idler gear to synchronously or asynchronously adjust a stroke and rotation. Furthermore, some embodiments embrace a particular system that is configured to synchronously reciprocate or asynchronously reciprocate as desired by the user.

Figure 15:
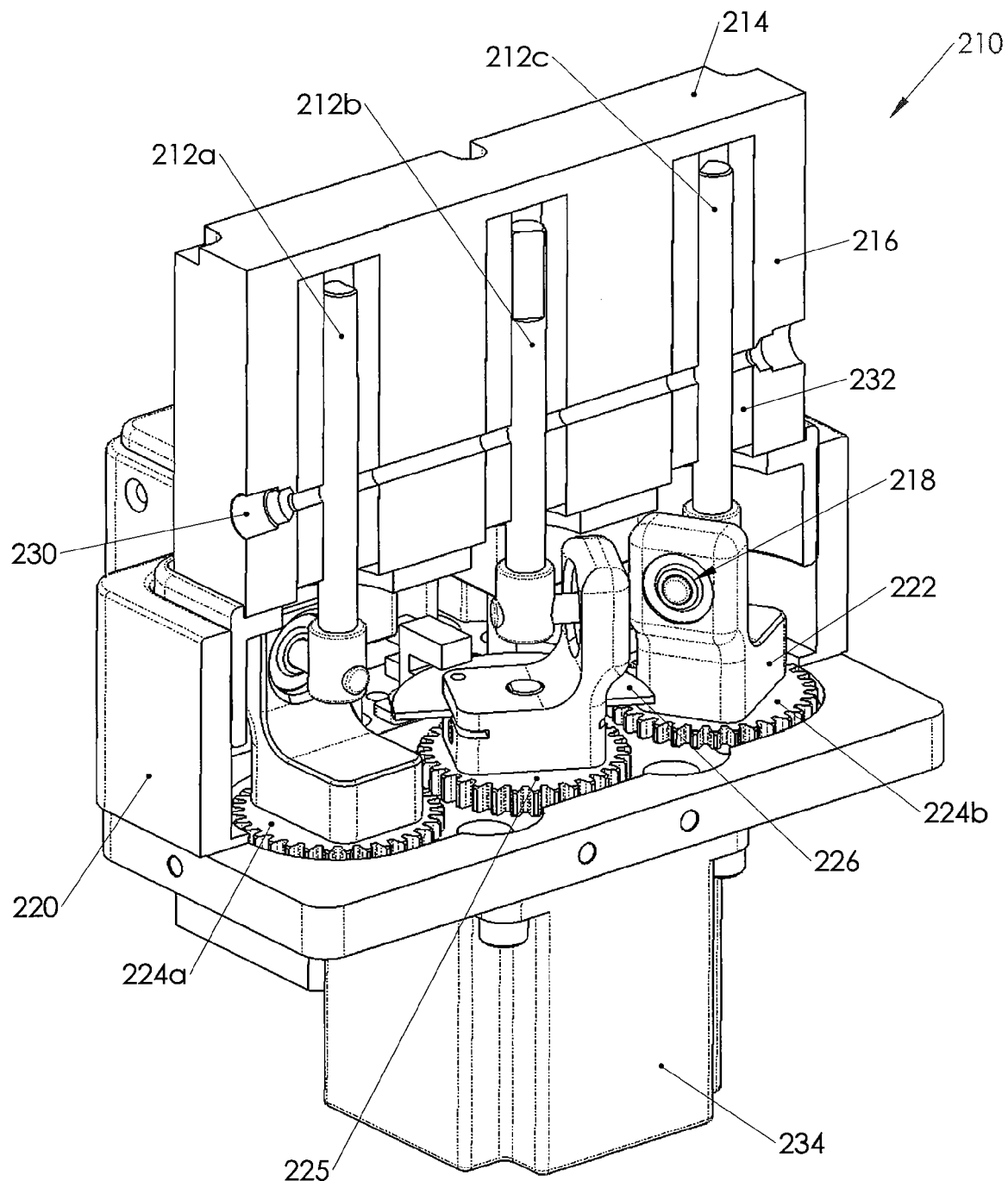
FIG. 15 illustrates a representative reciprocating fluid dispenser having a plurality of pistons.

Moreover, some embodiments of the present invention include a plurality of pistons. For example, reference is made to FIG. 15, wherein a representative reciprocating fluid dispenser having a plurality of pistons is illustrated. In FIG. 15, fluid dispenser 210 includes a plurality of pistons 212, cylinder cap 214, cylinder housing 216, spherical bearing 218, pump housing 220, spindle 222, idler pulleys 224, drive pulley 225, sensor flag 226, drive/timing belt 228, wash port 230, cylinder liner 232, and motor 234. In FIG. 15, pistons 212 are 120° out of phase to reduce/eliminate pulsing and to provide for a continuous flow as a positive volumetric pump.

While the embodiment of FIG. 15 includes three pistons, those skilled in the art will appreciate that embodiments of the present invention embrace less than three pistons or more than three pistons.

Furthermore, while reference has been made to linear actuators, at least some embodiments of the present invention utilize servo motors.

Thus, as discussed herein, embodiments of the present invention embrace accurately and repeatably dispensing fluid. In particular, the present invention relates to systems and methods for providing a dynamically adjustable reciprocating fluid dispenser.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A reciprocating fluid dispensing system configured to selectively dispense a precise and repeatable volume of fluid, the system comprising:
   a reciprocating fluid pump having a pump shaft and a pump cylinder;
   a pump drive motor coupled to the reciprocating fluid pump to selectively actuate the pump shaft within the pump cylinder; and
   an electrical adjustment mechanism coupled to the reciprocating fluid pump to precisely and repeatably adjust a stroke of the pump shaft, the electrical adjustment mechanism comprising:
      a linear actuator having a first surface defining a first plane and a screw extending outwardly from the first surface of the linear actuator, the screw generally defining a normal vector to the first plane;
      a slide having a sleeve element which slides on a guide rod, the sleeve being coupled to the linear actuator via the screw:
      a generally cylindrical cam follower element rotatable about an axis that is generally parallel the first plane; and
      a hinge block, wherein the sleeve element is coupled to the cam follower, and the hinge block includes a race configured to receive a bearing surface of the cam follower.

2. A reciprocating fluid dispensing system as recited in claim 1, wherein the pump shaft includes a duct that enables ingress of the precise and repeatable volume of fluid into the fluid pump from a fluid source and subsequent egress of the precise and repeatable volume of fluid from the fluid pump to a dispense target.

3. A reciprocating fluid dispensing system as recited in claim 1, wherein the reciprocating fluid pump is a synchronous reciprocating fluid dispenser.

4. A reciprocating fluid dispensing system as recited in claim 1, wherein a position of the sleeve element is controlled by the linear actuator.

5. A reciprocating fluid dispensing system as recited in claim 1, wherein the electrical adjustment mechanism further includes a compensation spring that provides a bias on the hinge block.

6. A reciprocating fluid dispensing system as recited in claim 5, wherein the compensation spring compensates for clearance between the bearing surface of the cam follower and the race.

7. A reciprocating fluid dispensing system as recited in claim 5, wherein the compensation spring bias compensates for a backlash in the linear actuator.

8. A reciprocating fluid dispensing system as recited in claim 1, wherein the sleeve element is configured to move freely along the guide rod.

9. A reciprocating fluid dispensing system as recited in claim 1, wherein a portion of the screw is coupled to the sleeve element.

10. A reciprocating fluid dispensing system as recited in claim 1, wherein the guide rod comprises a plurality of guide rods.

11. A reciprocating fluid dispensing system configured to selectively dispense a precise and repeatable volume of fluid, the system comprising:
   a reciprocating fluid pump having a pump shaft and a pump cylinder;
   a pump drive motor coupled to the reciprocating fluid pump to selectively actuate the pump shaft within the pump cylinder;
   an electrical adjustment mechanism coupled to the reciprocating fluid pump to precisely and repeatably adjust a stroke of the pump shaft, the electrical adjustment mechanism comprising:
      a linear actuator having a screw extending outwardly from the linear actuator, the screw being rotatable about a first axis;
      a slide having a sleeve element which slides on a guide rod, the sleeve being coupled to the linear actuator via the screws;
      a cam follower, rotatable about a second axis, the second axis being generally perpendicular to the first axis; and
      a hinge block, wherein the sleeve element is coupled to the cam follower, and the hinge block includes a race configured to receive a bearing surface of the cam follower.

12. A reciprocating fluid dispensing system as recited in claim 11, wherein the pump shaft includes a duct that enables ingress of the precise and repeatable volume of fluid into the fluid pump from a fluid source and subsequent egress of the precise and repeatable volume of fluid from the fluid pump to a dispense target.

13. A reciprocating fluid dispensing system as recited in claim 11, wherein a position of the sleeve element is controlled by the linear actuator.

14. A reciprocating fluid dispensing system as recited in claim 11, wherein the electrical adjustment mechanism further includes a compensation spring that provides a bias on the hinge block.

15. A reciprocating fluid dispensing system as recited in claim 14, wherein the compensation spring bias compensates for clearance between the bearing surface of the cam follower and the race.

16. A reciprocating fluid dispensing system as recited in claim 14, wherein the compensation spring compensates for a backlash in the linear actuator.

17. A reciprocating fluid dispensing system as recited in claim 11, wherein the sleeve element is configured to move freely along the guide rod.

18. A reciprocating fluid dispensing system as recited in claim 11, wherein a portion of the screw is coupled to the sleeve element.

19. A reciprocating fluid dispensing system as recited in claim 11, wherein the guide rod comprises a plurality of guide rods.

* * * * *